United States Patent [19]

Strong et al.

[11] 3,995,063

[45] Nov. 30, 1976

[54] INSECTICIDAL 1,1-DIPHENYL-2-NITROALKANES

[75] Inventors: Jerry G. Strong, Warren; Harold A. Kaufman, Piscataway, both of N.J.

[73] Assignee: Mobil Oil Corporation, New York, N.Y.

[22] Filed: Sept. 12, 1975

[21] Appl. No.: 612,597

Related U.S. Application Data

[63] Continuation-in-part of Ser. No. 410,935, Oct. 29, 1973, abandoned.

[52] U.S. Cl. ............................ 424/340; 260/612 R; 424/354
[51] Int. Cl.² ........................................... A01N 9/24
[58] Field of Search ................ 260/612 R; 424/340, 424/349, 354

[56] References Cited

UNITED STATES PATENTS

| | | | |
|---|---|---|---|
| 2,397,802 | 4/1946 | Müller | 260/64.5 |
| 2,516,186 | 7/1950 | Hass | 260/645 |
| 2,653,896 | 9/1953 | Hodges | 260/645 |
| 2,716,627 | 8/1955 | Johnson | 424/349 |

OTHER PUBLICATIONS

Bull. Wld. Hlth. Org. 33:633–647 (1968).

Metcalf et al., Bull. W. H. O. 44:363–374 (1971).

Hass et al., Ind. Eng. Chem. 43 2875–2878 (1951).

Jacob et al., J. Org. Chem. 16 1572–1576 (1951).

*Primary Examiner*—Leonard Schenkman
*Attorney, Agent, or Firm*—Charles A. Huggett; Hastings S. Trigg

[57] ABSTRACT

1,1-diphenyl-2-nitroalkanes, p-$C_4$–$C_6$ alkyl, p'-ethoxy substituted, are novel compounds which combine broad range insecticidal activity coupled with biodegradability and environmental safety.

28 Claims, No Drawings

INSECTICIDAL 1,1-DIPHENYL-2-NITROALKANES

CROSS-REFERENCE TO RELATED APPLICATIONS

This is a continuation-in-part of Ser. No. 410,935, filed Oct. 29, 1973, entitled 1,1-Diphenyl-2-Nitroalkanes and now abandoned.

BACKGROUND OF THE INVENTION

1. Field of the Invention

This invention is directed toward novel compounds of 1,1-diphenyl-2nitroalkanes, i.e., nitropropanes and nitrobutanes, substituted at their respective para-positions by $C_4$–$C_6$ alkyl and ethoxy, having utility as insecticides which are highly effective in combatting various difficult to control insect species such as lepidoptera, e.g., southern armyworm.

2. Description of the Prior Art

Since the discovery of the insecticidal properties of DDT, scientists have attempted to identify materials which are as effective as DDT and related chlorinated hydrocarbons but which are also biodegradable in living systems to excretable metabolites.

Attempts at accomplishing this goal by substituting alkyl and alkoxy substituents for chlorine in the basic diphenyl structure of DDT and related chlorinated hydrocarbons have been reported in the literature.

Thus the goal of identifying biodegradable insecticides structurally similar to DDT has been achieved, but none of the compounds reported exhibit the same broad range of insecticidal effectiveness as DDT. Specifically, none of the reported biodegradable DDT - like insecticides, e.g., diphenylalkanes containing an alkoxy or alkyl substituent, is effective at low application rates (100 ppm or less) on, for example, the important agronomic class of insects, lepidoptera.

For example, methoxychlor which represents the DDT basic structure with methoxy groups in the p,p' positions instead of chlorine as reported by I. P. Kapoor, et al., *J. Ag. Food Chem.*, 18, 1145 (1970) is biodegradable in living systems but has essentially no activity against the important lepidopterous insect, southern armyworm (See Table I below) even at the high rate of 500 ppm. R. L. Metcalf et al., *Bull. Wld. Hlth. Org.*, 44, 363 (1971), disclosed new biodegradable DDT analogues possessing p-alkyl, p'-alkoxy substituents in place of chlorine. The more insecticidally effective of these compounds reportedly was methyl methoxychlor and methyl ethoxychlor. Nevertheless, in our test (See Table I below) these compounds, at the high application rate of 500 ppm, did not control southern armyworm. T. A. Jacob et al., in *J. Org. Chem.* 16, 1572 (1951) reported that no activity was observed against the southern armyworm when p,p' - alkoxy substituted diphenyl-nitroalkanes were used as insecticides.

Additionally, U.S. Pat. No. 2,716,627 discloses 1-aryl derivatives of 2-nitro-1-p-isopropylphenylalkanes as being adapted to combat insects including the southern armyworm. However test data reported in said patent on representative compounds, e.g., 2-nitro-1-p-isopropylphenyl-1-p-ethylphenylbutane, 2-nitro-1,1-bis-(p-isopropylphenyl)butane and 2-nitro-1-p-isopropylphenyl-1-tolylbutane revealed that in fact insecticidal compositions containing same were totally ineffective having zero percent kill at application rates of 100 ppm against southern armyworm larvae. Testing these compounds under the same test conditions as the compounds according to this invention revealed essentially the same results, i.e., compositions containing compounds embodied in U.S. Pat. No. 2,716,627 showed little or no effect on southern armyworm larvae.

Additionally, Metcalf et al. *Bull Wld. Hlth. Org.*, 38, 633–647, (1968) in evaluating the relationship of chemical structure to the mode of action of DDT and DDT-like compounds and to the mechanisms of insect resistance to DDT and DDT-like compounds positively state that insect activity of such compounds is optimal when the phenyl groups thereof are substituted by small relatively non-polar groups such as $CH_3$, $CH_3O$, $C_2H_5$ and $C_2H_5O$. Metcalf et al., further positively state that when these compounds have phenyl substituents with larger alkyl groups in the p and p' positions, that is larger than $C_2H_5$, they were found to be completely insecticidally inactive.

Thus the prior art indicates that DDT-type compounds possessing alkoxy and alkyl substituents would be biodegradable but would most likely be unable to control, for example, the lepidopterous class of insects at economic levels of application, particularly where alkyl substituents are larger than $C_2H_5$. Therefore, quite unexpectedly and in sharp contradistinction to these hypotheses, the novel compounds of this invention while possessing the biodegradable p-alkoxy and p-alkyl substituents and a large ($C_4$) alkyl group are nevertheless most effective in controlling a broad specctrum of insects, e.g., the lepidoptera insect species, highly destructive of important field crops. Effective control of this class of insects, e.g., the southern armyworm has been obtained at the low economic application rate of 100 ppm.

SUMMARY OF THE INVENTION

This invention provides a new class of compounds having the following general structure:

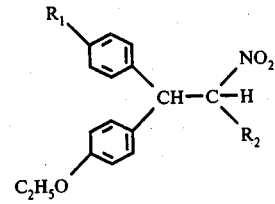

wherein $R_1$ is $C_4$–$C_6$ alkyl, branched or unbranched, e.g., $R_1$ may be n-butyl, sec-butyl, isobutyl or tertiary-butyl, and t-amyl and wherein $R_2$ is methyl or ethyl. Thus, embodiments include compounds wherein $R_2$ is ethyl and $R_1$ is a $C_4$ alkyl from the group consisting of n-butyl, sec-butyl, isobutyl and tertiary butyl.

This invention also provides for the use of these compounds in combatting insects and for insecticidally effective compositions of matter comprising at least one such compound as insect-control agent. Unlike DDT and other related chlorinated hydrocarbons, these compounds contain moities which render them biodegradable and non-persistant in the environment. R. L. Metcalf et al. report in the *Bull. Wld. Hlth. Org.*, 44, 363 (1971) that DDT analogues having substituent groups (e.g., alkoxy and alkyl) are readily attacked by multi-function oxidaze enzymes present in the environment, and undergo substantial biological degradation and do not appear to be readily stored or concentrated in animal tissues or food chains. Additionally, the compounds embodied herein are broadly effective in insecticidal activity against lepidoptera (e.g., southern armyworm) and coleoptera, (e.g., Mexican bean beetle) the two major classes of insects in terms of the annual amount of damage they inflict upon food crops. These compounds are also broadly effective in insect activity at low application rates, being particularly effective against the difficult to control southern armyworm even at application rates as low as 100 ppm or 0.01%, i.e., by weight of the insect-control agent in the composition thereof with a carrier.

DESCRIPTION OF PREFERRED EMBODIMENTS

As will be noted from the structural formula given above, the compounds according to this invention are 1,1-diphenyl-2-nitropropanes or butanes. Non-limiting examples of compounds of this invention include: 1-(p-tert-Butylphenyl)-1-(p-ethoxyphenyl)-2-nitrobutane; 1-(p-tert-Butylphenyl)-1-(p-ethoxyphenyl)-2-nitropropane; 1-(p-Isobutylphenyl)-1-(p-ethoxyphenyl)-2-nitropropane; 1-(p-Isobutylphenyl)-1-(p-ethoxyphenyl)-2-nitrobutane; 1-(p-sec-Butylphenyl)-1-(p-ethoxyphenyl)-2-nitropropane; 1-(p-sec-Butylphenyl)-1-(p-ethoxyphenyl)-2-nitrobutane; 1-(p-n-Butylphenyl-1-(p-ethoxyphenyl)-2-nitrobutane; 1-(p-n-Butylphenyl)-1-(p-ethoxyphenyl)-2-nitropropane, 1-p-tert-.amylphenyl)-1-(p-ethoxyphenyl) 2-nitrobutane, 1-(p-tert.amylphenyl)-1-(p-ethoxyphenyl)-2-nitropropane, and others.

In general, the compounds according to this invention are prepared by condensing ethoxybenzene (phenetole) with 2-nitro-1-p-$C_4$–$C_6$ alkylphenyl-1-alkanol in the presence of sulfuric acid. A solvent such as acetic acid, carbon tetrachloride, ethylene dichloride or water may be employed. Excess phenetole may also serve as solvent. The temperature of the reaction may vary from a −10° to a +50° C.

The starting materials (phenetole and sulfuric acid) are commercially available. The 2-nitro-1-p-$C_4$–$C_6$-alkylphenyl-1-alkanols may be prepared by condensing p-alkylbenzaldehydes with a 1-nitroethane or 1-nitropropane according to standard known procedures as illustrated below. The nitroalkanes are commercially available. The p-alkyl-benzaldehydes may be prepared according to the procedure of A. Reiche, H. Gross and E. Hoft, Ber., 93, 88 (1960) from commercially available alkylbenzenes.

Examples 1 through 5 illustrate a convenient method of preparing nitroalkanols useful in the preparation of diphenyl alkanes (Examples 6 to 10) in accordance with the invention and the comparative diphenyl alkanes of Examples 11 and 12. Further, Examples 13 through 15 illustrate a convenient method of preparing nitroalkanols useful in the preparation of comparative additional diphenylalkanes, i.e. Examples 16 through 21. The comparative 1,1-diphenyl-2-nitroalkanes (Examples 10, 11, 12 and 16–21) were prepared for screening in standard greenhouse insecticide evaluations under test conditions identical to those to which the compounds in accordance with the invention (Example 6–10) were subjected.

EXAMPLE 1

2-nitro-1-(p-tert-butylphenyl)-1-butanol

A 81 g portion of p-tert-butylbenzaldehyde was added portionwise over 0.5 hour to a vigorously stirred solution of 57 g of sodium bisulfite in 500 ml of water and 200 ml of 95% ethanol. The resulting heterogeneous mixture was stirred overnight at ambient temperature. In a separate flask 89 g of 1-nitropropane were added slowly at 5° C to a solution of 40 g of sodium hydroxide in 250 ml of 95% ethanol and 50 ml of water. The resulting yellow solution was stirred at ambient temperature for 0.5 hr. before it was added dropwise to the above heterogeneous mixture at 5° C with vigorous stirring. The resulting slurry was then stirred overnight at ambient temperature. The reaction mixture was filtered to remove a white solid precipitate, and the filtrate was diluted with 500 ml of water and extracted with 3 × 200 ml of ethyl ether. The ethereal solution was washed with water and with saturated aqueous bicarbonate and then stirred with saturated sodium bisulfite until all unreacted benzaldehyde was removed as an insoluble bisulfite salt. The remaining ethereal solution was dried over magnesium sulfate and then concentrated under vacuum to remove solvent and unreacted 1-nitropropane. The residue which crystallized on trituration with hexane was recrystallized from hexane to afford 40 g of product: mp 86°–88°; ir (KBr) 2.8 (s), 3.4 (s), 6.5 (s), 7.3 (s), 9.4 (m), 11.9 (s), 12.4 (m) microns; nmr (CDCl$_3$) 7.55 to 7.20 (4H), 4.7 to 4.4 (1H, m); 4.4 to 4.2 (1H, t), 3.0 (1H, broad), 1.95 (2H, m), 1.3 (9H, s), 0.8 (3H, m) ppm.

EXAMPLE 2

2-nitro-1-(p-tert-butylphenyl)-1-propanol

The procedure of Example 1 was followed using 81 g of p-tert-butylbenzaldehyde, 57 g of sodium bisulfite, 75 g of 1-nitroethane and 40 g of sodium hydroxide with ethanol and water as solvents. The final product was recrystallized from hexane to provide 33 g of white crystals: mp 79°–88°; ir (KBr) 2.8 s), 3.4 (s), 6.4 (s), 7.35 (m), 9.8 (m), 11.9 (s), microns; nmr (CDCl$_3$) 7.45 to 7.15 (4H, m) 5.0 to 4.6 (2H, m), 2.8 (1H, broad), 1.3 (6H, s), 1.4 to 1.2 (3H, d) ppm.

EXAMPLE 3

2-nitro-1-(p-n-butylphenyl)-1-butanol

A 1.5 ml portion of 3.7N potassium hydroxide in ethanol was added dropwise to a stirred, cooled (0°–5° C) solution of 11.2 g of p-n-butylbenzaldehyde and 24 g of 1-nitropropane in 2.5 ml of ethanol. After 2 hours at 0°–5° C, 1 ml of glacial acetic acid was added and the organic products were extracted into ethyl ether (100 ml). The ethereal solution was washed with water, with satd. sodium bicarbonate and with brine and then stirred overnight with a solution of 40 g sodium bisulfite in 100 ml water and 30 ml methanol. The organic phase was dried over magnesium sulfate and evaporated to yield 16.2 g of a viscous liquid. Trituration with 20/40 pet ether at −10° C afforded 9.7 g of a white solid mp 56°–61° C; ir (KBr) 2.7 (m), 3.5 (s), 6.4 (i s), 7.3 (m), 9.7 (m), 11.9 (m), 12.4 (m) microns; nmr (CCl$_4$) 7.07 (4H, s), 4.82 (1H, d of d), 4.40 (1H, sextet), 3.12 (1H, d), 2.56 (2H, t) 1.90 to 1.10 (6H, m), 0.90 (3H, t), 0.79 (3H, t) ppm.

EXAMPLE 4

2-nitro-1-(p-sec-butylphenyl)-1-butanol

The procedure of Example 3 was followed for the reaction of 1.0 ml of 3.7N potassium hydroxide with 9.7 g of p-sec-butyl-benzaldehyde and 16.0 g of 1-nitropropane in 1.5 ml of ethanol. Obtained was 13.6 g of crude product which was crystallized from 30 ml of 20/40 pet ether at −10° C to afford 7.0 g of white powder: mp 59°–60° C; ir (KBr) 2.9 (s), 3.4 (s), 6.4 (s), 7.3 (m), 12.1 (m) microns; nmr (CCl$_4$) 7.09 (4H, q), 4.85 (1H, d of d), 4.4 (1H, sextet), 3.05 (1H, d), 2.60 (1H, m), 2.0 to 1.4 (4H, m) 1.19 (3H, d), 0.78 (6H, t) ppm.

EXAMPLE 5

2-nitro-1-(p-isobutylphenyl)-1-butanol

The procedure of Example 3 was followed for the reaction of 5 ml of 3.7N potassium hydroxide with 16.2 g of p-isobutylbenzaldehyde and 26.7 g of 1-nitropropane in 7.5 ml of ethanol. Obtained was 20.0 g of a yellow viscous liquid which did not crystallize: ir (film) 2.8 (s), 3.4 (s), 6.4 (s), 7.3 (m), 9.7 (m), 12.4 (m) microns; nmr (CCl$_4$) 7.11 (4H, q), 4.84 (1H, d), 4.42 (1H, sextet), 3.15 (1H, s), 2.44 (2H, d), 1.75 (2H, m), 0.86 (6H, d), 0.83 (3H, t) ppm.

EXAMPLE 6

1-(p-tert-butylphenyl)-1-(p-ethoxyphenyl)-2-nitrobutane

To 90 ml portion of 98% sulfuric acid were slowly added 33 g of phenetole at 0° C. The solution was cooled to −15° C and a solution of 22.5 g of Example 1 in 66 g of phenetole was added dropwise over 1 hour at −5° to −10° C. The reaction solution was stirred at −5° C for 1.5 hr. and then poured into 1 liter of ice and water. The organic products were extracted into ethyl ether, and the ethereal solution was washed with water, saturated bicarbonate and brine, dried over magnesium sulfate and concentrated. Excess phenetole was removed at the vacuum pump leaving a semi-solid residue weighing 24 g. The residue was recrystallized twice from hexane to yield a purified sample: mp 95°–97°; ir (KBr) 3.4 (s), 6.7 (s), 7.3 (s), 8.0 (s), 9.6 (s), 12.2 (m) microns; nmr (CDCl$_3$) 7.3 to 7.0 and 6.9 to 6.6 (8H, m), 5.3 to 5.0 (1H, m), 4.2 (1H, d), 3.8 (2H, q), 1.7 (2H, broad), 1.2 (9H, s), 0.85 (3H, t) ppm; ms (molecular ion) 355.

EXAMPLE 7

1-(p-tert-butylphenyl)-1-(p-ethoxyphenyl)-2-nitropropane

A 1.0 kg portion of 80% sulfuric acid was added dropwise to a solution of 237 g of Example 2 in 732 g of phenetole and the mixture was heated to 50° C for 2 hr. The acid layer was removed and the organic phase was diluted with ether. The ethereal solution was washed with water and with saturated sodium bicarbonate, dried over magnesium sulfate and evaporated. The crude residue which weighed 322 g was triturated with 30/60 pet ether and the isolated solids were recrystallized from 30/60 pet ether and from isopropyl alcohol to afford a pure, white solid: mp 79°–82° C; ir (KBr) 3.4 (m), 6.5 (s), 6.6 (m), 8.0 (s), 9.5 (m), 12.2 (m) microns; nmr (CDCl$_3$) 7.4 to 6.7 (8H, m), 5.3 (1H, doublet of quarters), 4.3 (1H, d), 3.97 (2H, q), 1.45 (3H, d), 1.29 (3H, t), 1.22 (9H, s) ppm; ms (molecular ion) 341.

EXAMPLE 8

1-(p-n-butylphenyl)-1-(p-ethoxyphenyl)-2-nitrobutane

The procedure of Example 7 was followed for the reaction of 6.3 g of Example 3 and 18.2 g of phenetole with 25 g of 80% sulfuric acid. Obtained was 8.0 g of a viscous, yellow liquid which would not crystallize. The residue in 50 ml of 50:50 dichloromethane and hexane was filtered through 40 g of silica gel and eluted with 250 ml of the same solvent. Concentration of the solvent afforded 7.5 g of a clear, colorless liquid: ir (film) 3.4 (m), 6.4 (s), 6.7 (m), 8.0 (m), 9.6 (m) microns; nmr (CCl$_4$) 7.4 to 6.9 and 6.7 to 6.5 (8H, m), 5.07 (1H, d of q), 4.25 (1H, d), 3.76 (2H, q), 2.48 (2H, t), 2.0 to 1.1 (6H, m), 1.10 (3H, t), 0.84 (3H, t), 0.80 (3H, t) ppm.

EXAMPLE 9

1-(p-sec-butylphenyl)-1-(p-ethoxyphenyl)-2-nitrobutane

The procedure of Example 7 was followed for the reaction of 8.8 g of Example 4 and 18.2 g of phenetole with 25 g of 80% sulfuric acid. Obtained were 11.7 g of a yellow liquid which crystallized from 25 ml of 20/40 pet ether. The collected solid was recrystallized from methanol to afford 6.7 of white crystals: mp 89°–90° C; ir (KBr) 3.4 (m), 6.4 (a), 6.6 (s), 8.0 (s), 12.2 (m) microns; nmr (CCl$_4$) 7.2–6.5 (8H, m), 5.0 (1H, d of q), 4.21 (1H, d), 3.83 (2H, q), 2.48 (1H, sextet), 2.0 to 0.75 (16H, m) ppm.

EXAMPLE 10

1-(p-isobutylphenyl)-1-(p-ethoxyphenyl)-2-nitrobutane

The procedure of Example 7 was followed for the reaction of 7.5 g of Example 5 and 22 g of phenetole with 30 g of 80% sulfuric acid. Obtained were 10.9 g of a viscous liquid which crystallized from cold methanol to afford 4.5 g of a white powder: mp 68°–73° C; ir (KBr) 3.4 (m), 6.4 (s), 6.7 (s), 8.0 (s), 9.6 (m), 12.4 (m) microns; nmr (CCl$_4$) 7.56 (4H, dd), 6.88 (4H, dd), 5.00 (1H, sextet), 4.23 (1H, d), 3.90 (2H, q), 2.39 (2H, d), 1.7 to 2.0 (2H, m), 1.30 (3H, t), 0.86 (3H, t), 0.82 (6H, d) ppm.

COMPARATIVE EXAMPLES 11–21

EXAMPLE 11

1-(p-tert-butylphenyl)-1-(p-methoxyphenyl)-2-nitrobutane

The procedure of Example 6 was followed for the reaction of 22.5 g of Example 1 with 90 g of anisole and 90 ml of sulfuric acid, resulting in 20 g of crude product. A pure sample was obtained by recrystallization from heptane; mp 114–116° C; ir (KBr) 3.4 (m), 6.3 (m), 6.5 (s), 6.7 (m), 8.0 (s), 9.7 (m), 12.2 (m), 12.5 m) microns; nmr (CDCl$_3$) 7.4 to 7.1 and 6.85 to 6.7 (8H, m), 5.35 to 5.05 (1H, m) 4.3 (1H, d), 3.6 (3H, s), 1.95 to 1.65 (2H, m), 1.25 (9H, s), 0.9 (3H, t) ppm; ms (molecular ion) 298.

EXAMPLE 12

1-(p-tert-butylphenyl)-1-(p-methoxyphenyl)-2-nitropropane

The procedure of Example 6 was followed for the reaction of 7.1 g of Example 2 with 30 g of anisole and 30 ml of 98% sulfuric acid. The crude product (11 g) was obtained by filtration of the reaction mixture following mixture with ice and water. A purified sample was provided by recrystallization from ethanol; mp 155°–156.5° C; ir (Kbr) 3.35 (m), 6.5 (s) 6.6 (m), 8.05 (m), 9.7 (m), 12.2 (m) microns; nmr (CDCl$_3$) 7.35 to 7.05 and 6.95 to 6.7 (8H, m), 5.45 to 5.15 (1H, m), 4.3 (1H, d) 3.65 (3H, s), 1.65 to 1.35 (3H, m), 1.2 (9H, s) ppm.

EXAMPLE 13

2-nitro-1-(p-tolyl)-1-propanol

The procedure of Example 1 was followed for the reaction of 120 g of p-tolualdehyde and 114 g of sodium bisulfite with 150 g of 1-nitroethane and 80 g of sodium hydroxide. Water was the solvent. The final product was a yellow liquid weighing 103 g: ir (film) 2.85 (m), 3.4 (m), 6.5 (s), 7.2 (m), 7.35 (m), 9.5 (m), 12.15 (m) microns; nmr (CDCl$_3$) 7.12 (4H, s), 5.0 to 4.5 (2H, m), 2.95 (1H, s), 2.3 (3H, s), 1.4 and 1.2 (3H, doublet and doublets) ppm.

EXAMPLE 14

2-nitro-1-(p-tolyl)-1-butanol

The procedure of Example 1 was followed for the reaction of 120 g of p-tolualdehyde and 114 g of sodium bisulfite with 178 g of 1-nitropropane and 80 g of sodium hydroxide. Water and ethanol were the solvents. The product obtained was a clear, yellow liquid weighing 100 g; ir (film) 2.8 (s), 3.4 (m), 6.5 (s), 7.3 (m), 9.7 (m), 12.2 (s) microns.

EXAMPLE 15

2-nitro-1-(p-isopropylphenyl)-1-propanol

The procedure of Example 1 was followed for the reaction of 74 g of p-isopropylbenzaldehyde and 57 g of sodium bisulfite with 75 g of 1-nitroethane and 40 g of sodium hydroxide. Water and ethanol served as solvents. The product weighed 41 g and was a light yellow oil which slowly crystallized on standing: ir (film) 2.85 (m), 3.35 (m), 6.5 (s), 7.2 (m), 7.35 (m), 9.5 (m), 11.95 (m) microns; nmr (CDCl$_3$) 7.1 (4H, s), 5.0 to 4.6 (2H, m) 3.05 (1H, broad), 2.9 (1H, quintet), 1.3 (6H, d), 1.5 to 1.2 (3H, m) ppm.

EXAMPLE 16

1-(p-tolyl)-1-(p-ethoxyphenyl)-2-nitrobutane

The procedure of Example 6 was followed for the reaction of 16.6 g of Example 14 with 55 g of phenetole and 50 ml of sulfuric acid. The crude product was recrystallized from hexane to afford 8 g of white crystals: mp 92°–94°; ir (KBr) 3.4 (m), 6.5 (s), 6.7 (m), 8.0 (s), 9.5 (m), 12.2 (m) microns; nmr (CDCl$_3$) 7.3 to 7.1 and 6.85 to 6.7 (8H, m), 5.3 to 5.0 (1H, m), 4.3 (1H, d) 3.93 (2H, q), 2.27 (3H, s), 1.95 to 1.65 (2H, m) 1.32 (3H, t), 1.02 (3H, t) ppm.

EXAMPLE 17

1-(p-tolyl)-1-(p-ethoxyphenyl)-2-nitropropane

The procedure of Example 6 was followed for the reaction of 15.6 g of Example 13 and 55 g of phenetole in 50 ml of 98% sulfuric acid. The product weighed 15 g and was a viscous liquid: ir (film) 3.4 (m), 6.5 (s), 6.65 (s), 8.05 (s), 9.55 (m), 12.3 (m) microns; nmr (CDCl$_3$) 7.3 to 6.6 (8H, m), 5.4 to 5.15 (1H, m), 4.3 (1H, d), 3.85 (2H, m), 2.2 (3H, s), 1.4 (3H, t), 1.25 (3H, t) ppm.

EXAMPLE 18

1-(p-tolyl)-1-(p-anisyl)-2-nitropropane

The procedure of Example 6 was followed for the reaction of 15.6 g of Example 13 with 49 g of anisole and 50 ml of 98% sulfuric acid. Obtained was 11.3 g of product as a viscous liquid: ir (film) 3.4 (m), 6.45 (s), 6.65 (m), 8.0 (s), 8.5 (m), 9.7 (s), 12.3 (m) microns; nmr (CDCl$_3$) 7.3 to 6.7 (8H, m), 5.3 (1H, doublet of quartets), 4.3 (1H, doublet), 3.6 (3H, s), 2.2 (3H, s), 1.42 (3H, d) ppm.

EXAMPLE 19

1-(p-isopropylphenyl)-1-(p-anisyl)-2-nitropropane

The procedure of Example 6 was followed for the reaction of 6.7 g of Example 15 with 30 g of anisole and 30 ml of 98% sulfuric acid. The product was recrystallized from hexane to afford 4.3 g of a white solid; mp 112°–115° C; ir (KBr) 3.5 (s), 6.5 (s), 6.7 (m), 8.0 (s), 9.5 (m), 12.3 (m) microns; nmr (CDCl$_3$) 7.15 (s) and 6.75 (d) (8H, aromatic), 4.3 (1H, quintet), 4.3 (1H, d) 3.7 (3H, s), 2.85 (1H, quintet), 1.48 (3H, d), 1.2 (6H, d) ppm.

EXAMPLE 20

1-(p-isopropylphenyl)-1-(p-ethoxyphenyl)-2-nitropropane

The procedure of Example 6 was followed for the reaction of 6.7 g of Example 15 with 33 g of phenetole and 30 ml of 98% sulfuric acid. The product weighed 5 g and remained as a viscous, amber liquid: ir (film) 3.4 (s), 6.5 (s), 8.05 (s), 9.55 (s), 12.15 (m) microns; nmr (CDCl$_3$) 7.3 to 7.0 and 6.85 to 6.65 (8H, m), 5.3 (1H, doublet of quartets), 4.3 (1H, doublet), 3.85 (2H, q), 2.82 (1H, quintet), 1.6 to 1.0 (12H, m) ppm.

EXAMPLE 21

1-(p-isopropylphenyl)-1-(p-ethoxyphenyl)-2-nitrobutane

The procedure of Example 6 was followed for the reaction of 11.9 g of Example 15 with 24.4 g of phenetole, 20 ml of 98% sulfuric acid and 20 ml of carbon tetrachloride. The product weighed 14 g and remained as a clear, amber, viscous liquid: ir (film) 3.4 (s), 6.5 (s), 8.1 (s), 9.6 (s), 12.2 (s), 12.4 (m), microns; nmr (CDCl$_3$) 7.3 to 6.7 (8H, m), 5.2 (1H, doublet of quartets), 4.3 (1H, doublet), 3.9 (2H, q), 2.83 (1H, quintet), 1.78 (2H, m), 1.5 to 1.05 (9H, m), 0.9 (3H, t) ppm.

EXAMPLE 22

In this example the nitroalkanes prepared above i.e., Examples 6–10 according to the invention and Comparative Examples 11, 12 and 16 to 21 were evaluated in standard greenhouse insecticide tests using housefly (HF), bean aphid (BA), Mexican bean beetle (MB), southern armyworm (SA) and yellow fever mosquito (YF). The rates of application were 500 and 100 ppm of active ingredient except in the case of yellow fever mosquito where test rates were 10 and 1 ppm of active ingredient. The results as set forth in Table I below indicate the percent kill of each insect species. Standard DDT type compounds: methoxychlor, methyl methoxychlor and methyl ethoxychlor were also evaluated under identical test conditions. Comparative Examples 11 and 12 were evaluated to illustrate the comparative effectiveness of 1,1-diphenylnitroalkanes having a methoxyphenyl rather than the ethoxyphenyl radical of the compounds of this invention. Comparative Examples 16 and 17, and Examples 20 and 21 were evaluated to illustrate the performance of such alkanes where the butyl radical of compounds in accordance with this invention was replaced by a methyl group (Ex. 16 and 17) and an isopropyl group (Ex. 20 and 21); Examples 18 and 19 were evaluated to illustrate the performance of compounds where the butylphenyl and the ethoxyphenyl groups were replaced in Example 18 by methylphenyl and methoxyphenyl; and in Example 19 by isopropylphenyl and methoxyphenyl.

TEST METHODS

Housefly; 1 milliliter of an aqueous solution or suspension of the test compound was pipeted into a 9 cm. petri dish containing filter paper and 0.1 gram of granular sugar. Ten adult houseflies were admitted and the dish closed. Observations were made periodically for knockdown and at 24 hours for mortality. Mortality was primarily caused by stomach poisoning.

Bean aphid; adult bean aphids on nasturtium cuttings were confined in specially designed 100 millimeter screened cages and exposed to sprays at 15 psi of 10.0 milliliters of an acetone solution of the test compound. The test cages were mounted on a turntable rotating at 30 rpm in a wind tunnel. When dry, the petioles of the treated leaves were placed in a water-filled plastic container on a specially constructed holding stand. This was necessary in order to keep the treated leaves turgid for the duration of the test. All the tests were run in duplicate with ten or more aphids in each cage. An initial concentration of 500 ppm was used and then the candidate compound was retested at 100 ppm. Mortality was recorded after 24 hours, with all tests run in duplicate.

Southern armyworm and Mexican bean beetle; lima bean leaves of uniform size were momentarily dipped in a water-acteone solution of the test compound and the treated leaves were then placed on moistened filter paper in 9 cm. petri dishes and allowed to air dry. When dry, five, third, or fourth instar larvae were introduced and encouraged to feed on the treated foliage by means of confinement. The dishes were closed and held for observation of mortality and feeding during a 48 to 72 hour period.

Yellow fever mosquito; fourth stage larvae were exposed to a solution of the active compound in water. The active material was initially dissolved in acetone and then added to the water. The compounds were screened initially at 10 ppm using approximately 10 larvae per 100 ml of treated water. Each treatment was replicated twice. Mortality was determined after 24 hour exposure.

TABLE 1

| Alkanes in Accordance with The Invention | | INSECTICIDAL EVALUATION OF 1,1-DIPHENYL-2-NITROALKANES | | | | |
|---|---|---|---|---|---|---|
| COMPOUND | RATE (ppm) | HF | BA | MB | SA | YF* |
| Example 6 | 500 | 100 | 70 | 100 | 100 | 100 |
|  | 100 | 100 | 40 | 100 | 100 | 80 |
| Example 7 | 500 | 100 | 100 | 100 | 100 | 100 |
|  | 100 | 100 | 100 | 100 | 80 | 100 |
| Example 8 | 500 | 100 | — | 100 | 100 | 100 |
|  | 100 | 100 | — | 100 | 90 | 100 |
| Example 9 | 500 | 100 | — | 100 | 100 | 100 |
|  | 100 | 30 | — | 100 | 90 | 20 |
| Example 10 | 500 | 100 | — | 100 | 100 | 100 |
|  | 100 | 90 | — | 100 | 100 | 80 |
| Comparative Compounds | | | | | | |
| Example 11 | 500 | 10 | 80 | 100 | 50 | 60 |
|  | 100 | — | 60 | 100 | 10 | 0 |
| Example 12 | 500 | 80 | 10 | 40 | 10 | — |
|  | 100 | — | — | — | — | — |
| Example 16 | 500 | 100 | 70 | 100 | 10 | 100 |
|  | 100 | — | 10 | 40 | — | — |
| Example 17 | 500 | 100 | 10 | 100 | 10 | 100 |
|  | 100 | — | — | 100 | — | — |
| Example 18 | 500 | 100 | 10 | 100 | 10 | 100 |
|  | 100 | — | — | 50 | — | — |
| Example 19 | 500 | 100 | 10 | 100 | 10 | 100 |
|  | 100 | — | — | 60 | — | 100 |
| Example 20 | 500 | 100 | 90 | 100 | 80 | 100 |
|  | 100 | — | 10 | 100 | 10 | 100 |
| Example 21 | 500 | 100 | 100 | 100 | 100 | 100 |
|  | 100 | 100 | — | 100 | 40 | 100 |
| DDT Analogues | | | | | | |
| Methoxychlor | 500 | 30 | 100 | 100 | 10 | 100 |
|  | 100 | — | 10 | 100 | 10 | 100 |
| Methyl methoxychlor | 500 | 100 | 100 | 100 | 10 | — |
|  | 100 | 10 | 10 | 100 | 10 | — |
| Methyl ethoxychlor | 500 | 90 | 100 | 100 | 10 | — |
|  | 100 | 10 | 10 | 100 | 10 | — |

*See remarks under Example 22 for application rate.

From the preceding data in the Table, it will be noted (1) that compounds embodied by the present invention have a broad range of insect-control activity, and also exhibit considerable insect-control activity at low rates of application, i.e., 100 ppm. (2) the DDT-type compounds, e.g., methoxychlor for all practical purposes did not exhibit a broad range of insect-control activity and were essentially ineffective against southern armyworm evan at the high application rates (500 ppm). In particular, the compounds of Example 6 thru 10 were markedly effective against southern armyworm at low application rates, i.e., 80 to 100% effective at 100 ppm. It is particularly noted that only those of the Examples that are compounds embodying the specific combination of p-$C_4$ alkylphenyl and p-ethoxyphenyl are substantially consistent in being highly effective against a broad range of insect species at low application rates. For example, the compound of Example 6, 1-(p-tert-butylphenyl)-1-(p-ethoxyphenyl)-2-nitrobutane is 100% effective against the difficult to kill southern armyworm at the low application rate of 100 ppm, as is the compound of Example 10, i.e., 1-(p-isobutylphenyl)-1-(p-ethoxyphenyl)-2-nitrobutane; and the compounds of Example 7 and 8 are 100% effective at an extremely low application rate against deadly yellow fever mosquito at 1 ppm. Combinations of the Examples other than those containing the $C_4$-alkylphenyl and ethoxyphenyl are much less effective, as for example, against southern armyworm. For example, the compound of Example 11, 1-(p-tert-butylphenyl-1-(p-methoxyphenyl)-2-nitrobutane is essentially ineffective against the aforementioned difficult to kill southern armyworm at an application rate of 100 ppm, while, for example, the compound of Example 6 which combines tert-butylphenyl and ethoxyphenyl is 100% effective at this application rate. Examples 11 and 12 wherein the p-$C_4$ alkyl radical in one of the rings is replaced by a $CH_3$ group are considerably less effective than compounds according to the invention. For example, the compounds of Examples 11 and 12 are essentially inactive against SA at the high application rate of 500 ppm whereas a compound of this invention (Example 6) has a 100% mortality rate against the difficult to kill SA at the low application rate of 100 ppm. This is in sharp contrast to the prior art in general and totally unexpected in view of the positive teaching of Metcalf et al. (1968) above that DDT-like compound with large alkyl groups in the p,p'position i.e., isopropyl, butyl, pentyl and dodecyl were completely insecticidally inactive.

Thus the foregoing data clearly illustrates, in example, the unexpected effectiveness of compounds according to the invention wherein the combination of $C_4$-alkylphenyl and ethoxyphenyl groups are utilized in 1,1-diphenyl-2-nitrobutanes or propanes.

In the production of the p-$C_4$-$C_6$ alkyl, p-ethoxy ring substituted compounds of this invention, the crude reaction product usually contains, in addition to the desired compounds, a minor amount of one or more isomers. Thus, for example and in regard to production of the compound of Example 6, i.e., 1-(p-tert.butylphenyl)-1-(p-ethoxyphenyl)-2-nitrobutane, the crude reaction product may comprise up to about 85% of the desired compound with the balance being mainly comprised of one or more isomers thereof, e.g., 1-(p-t-butylphenyl)-1-(o-ethoxyphenyl)-2-nitrobutane and stereoisomers of the desired compound. Similarly thereto are the reaction products for desired production of the other p-$C_4$ alkyl, p-ethoxy ring substituted nitrobutanes and nitropropanes embodied herein. Evaluations of such crude reaction compositions for insecticidal purposes, as compared to the substantially purified desired compound, have in general been found to provide substantially similar effectiveness. For example, a composition comprising about 85% of the compound of Example 6, about 10% of 1-(p-tert.butylphenyl)-1-(o-ethoxyphenyl)-2-nitrobutane and about 5% of the stereoisomer of the compound of Example 6 provided substantially the same effectiveness as the substantially pure Example 6 compound.

The compounds embodied herein may be used in various ways to achieve effective insect control. They can be applied per se, as solids or in vaporized form, but are preferably applied as the toxic components in insect control compositions of a compound and an inert solid or liquid carrier. The compositions can also be applied as dust, as liquid sprays, or as gas-propelled sprays and can contain, in addition to a carrier, additives such as emulsifying agents, wetting agents, binding agents, gases compressed through the liquid state, odorants, stabilizers and the like. A wide variety of liquid and solid carriers can be used in the insect-control compositions. Non-limiting examples of liquid carriers, include water; organic solvents such as alcohols, ketones, aliphatic and aromatic hydrocarbons, amides and esters; mineral oils such as kerosene, light oils, medium oils; and vegetable oils such as cottonseed oil. Non-limiting examples of solid carriers include talc, bentonite, diatomaceous earth, pyrophyllite, fullers earth, gypsum, flours derived from cottonseeds and nutshells, and various natural and synthetic clays having a pH not exceeding about 9.5.

The amount of compounds of this invention utilized in insect-control compositions will vary rather widely. It depends to some extent upon the type of composition in which the material is being used, the nature of the condition to be controlled, and the method of application (i.e. spraying, dusting, etc.). In the ultimate insect-control composition as applied in the field, insect-control agent concentrations as low as 0.0001 weight percent of the total composition can be used. In general, compositions containing from about 0.01–0.05 weight percent insect-control agent in either liquid or solid carrier give excellent results. In some cases, however, stronger dosages of up to about 80 weight percent may be required.

In practice compositions for controlling insects utilizing these compounds are usually prepared in the form of concentrates which are diluted in the field to the concentration desired for application. For example, the concentrate can be a wettable powder containing large amounts of a compound according to this invention, a carrier (e.g., attapulgite or other clay), and wetting and dispersing agents. Such a powder can be diluted prior to application by dispersing it in water to obtain a sprayable suspension containing the concentration of insect control agent desired for application. Other concentrates can be solutions that can be later diluted, e.g., with kerosene. Thus, it is within the contemplation of this invention to provide compositions combining superior insect activity with environmental safety. Such compositions may contain up to about 80%, by weight, of the composition of an insecticidally-active compound according to this invention. Accordingly, depending upon whether it is ready for application or it is in concentrated form the contemplated insect-control compositions may contain between about 0.0001 and about 80%, by weight of the composition, of an insecticidally-effective compound of this invention and a liquid or solid carrier as defined hereinabove.

13

Thus, the invention in addition to the new class of novel compounds described hereinabove also provides for a method of insect control comprising applying to the insect or its environment at least one compound of composition thereof according to this invention in effective amounts to obtain said control.

Although the present invention has been described with preferred embodiments, it is to be understood that modifications and variations may be resorted to while not departing from the spirit and scope of the invention.

What is claimed is:

1. A compound having the following general structure:

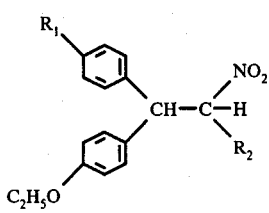

wherein $R_1$ is $C_4$ alkyl branched or unbranched and $R_2$ is methyl or ethyl.

2. A compound according to claim 1 wherein $R_1$ is tertiary-butyl and $R_2$ is ethyl.

3. A compound according to claim 1 wherein $R_1$ is tertiary-butyl and $R_2$ is methyl.

4. A compound according to claim 1 wherein $R_1$ is n-butyl and $R_2$ is ethyl.

5. A compound according to claim 1 wherein $R_1$ is n-butyl and $R_2$ is methyl.

6. A compound according to claim 1 wherein $R_1$ is sec-butyl and $R_2$ is ethyl.

7. A compound according to claim 1, wherein $R_1$ is sec-butyl and $R_2$ is methyl.

8. A compound according to claim 1 wherein $R_1$ is isobutyl and $R_2$ is ethyl.

9. A compound according to claim 1 wherein $R_1$ is isobutyl and $R_2$ is methyl.

10. An insecticidally effective composition comprising between about 0.0001 and about 80 weight percent, based on the weight of the total composition, of a compound according to claim 1 as the insecticide and an inert solid or liquid carrier therefor.

11. An insecticidally effective composition of claim 10, wherein 1-(p-tertiary-butylphenyl)-1-(p-ethoxyphenyl-2-nitrobutane is the insecticide.

12. An insecticidally effective composition of claim 10 wherein 1-(p-tertiary-butylphenyl)-1-(p-ethoxyphenyl)-2-nitropropane is the insecticide.

13. An insecticidally effective composition of claim 10, wherein 1-(p-n-butylphenyl)-1-(p-ethoxyphenyl)-2-nitrobutane is the insecticide.

14. An insecticidally effective composition of claim 10, wherein 1-(p-n-butylphenyl)-1-(p-ethoxyphenyl)-2-nitropropane is the insecticide.

15. An insecticidally effective composition of claim 10, wherein 1-(p-sec-butylphenyl)-1-(p-ethoxyphenyl)-2-nitrobutane is the insecticide.

16. An insecticidally effective composition of claim 10, wherein 1-(p-sec-butylphenyl)-1-(p-ethoxyphenyl)-2-nitropropane is the insecticide.

17. An insecticidally effective composition of claim 10, wherein 1-(p-isobutylphenyl)-1-(p-ethoxyphenyl)-2-nitrobutane is the insecticide.

18. An insecticidally effective composition of claim 10, wherein 1-(p-isobutylphenyl)-1-(p-ethoxyphenyl)-2-nitropropane is the insecticide.

19. A method of combatting insects comprising applying to the insects or to the environment of the insects an insecticidally effective amount of at least one compound having the following general structure:

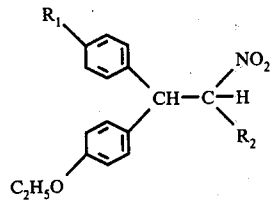

wherein $R_1$ is $C_4$ alkyl, branched or unbranched, and $R_2$ is methyl or ethyl.

20. The method of claim 19 in which said compound is 1-(p-tertiary-butylphenyl)-1-(p-ethoxyphenyl)-2-nitrobutane.

21. The method of claim 19 in which said compound is 1-(p-tertiary-butylphenyl)-1-(p-ethoxyphenyl)-2-nitropropane.

22. The method of claim 19 in which said compound is 1-(p-n-butylphenyl)-1-(p-ethoxyphenyl)-2-nitrobutane.

23. The method of claim 19 in which said compound is 1-(p-n-butylphenyl)-1-(p-ethoxyphenyl)-2-nitropropane.

24. The method of claim 19 in which said compound is 1-(p-sec-butylphenyl)-1-(p-ethoxyphenyl)-2-nitrobutane.

25. The method of claim 19 in which said compound is 1-(p-sec-butylphenyl)-1-(p-ethoxyphenyl)-2-nitropropane.

26. The method of claim 19 in which said compound is 1-(p-isobutylphenyl)-1-(p-ethoxyphenyl)-2-nitributane.

27. The method of claim 19 in which said compound is 1-(p-isobutylphenyl)-1-(p-ethoxyphenyl)-2-nitropropane.

28. A method for controlling Lepidopterous insects which comprises contacting said insects with a composition as defined in claim 10 in an amount sufficient to effect substantially complete control of said insect.

* * * * *